(12) United States Patent
Hur et al.

(10) Patent No.: US 8,165,688 B2
(45) Date of Patent: Apr. 24, 2012

(54) FREQUENCY ANALYZER FOR MEMS BASED COCHLEAR IMPLANT WITH SELF POWER SUPPLY

(75) Inventors: Shin Hur, Daejeon (KR); Wan-Doo Kim, Daejeon (KR)

(73) Assignee: Korea Institute of Machinery & Materials, Daejeon (KR)

( * ) Notice: Subject to any disclaimer, the term of this patent is extended or adjusted under 35 U.S.C. 154(b) by 784 days.

(21) Appl. No.: 12/257,089

(22) Filed: Oct. 23, 2008

(65) Prior Publication Data
US 2009/0112288 A1 Apr. 30, 2009

(30) Foreign Application Priority Data
Oct. 25, 2007 (KR) .................. 10-2007-0107648

(51) Int. Cl.
*A61N 1/00* (2006.01)
*A61B 5/04* (2006.01)
(52) U.S. Cl. ........... 607/57; 600/377; 600/379; 600/395
(58) Field of Classification Search .................. 607/57; 600/377, 379, 395; 205/775.5
See application file for complete search history.

(56) References Cited

U.S. PATENT DOCUMENTS

| 3,712,962 | A |  | 1/1973 | Epley |
| 3,764,748 | A |  | 10/1973 | Branch et al. |
| 4,885,781 | A |  | 12/1989 | Seidel |
| 6,092,422 | A |  | 7/2000 | Binnig et al. |
| 6,651,504 | B1 |  | 11/2003 | Datskos |
| 7,421,298 | B2 | * | 9/2008 | Daly et al. ...................... 607/57 |
| 2007/0256941 | A1 | * | 11/2007 | Prasad et al. ............... 205/775.5 |

FOREIGN PATENT DOCUMENTS

| JP | 58-002640 U | 1/1983 |
| JP | 11-502088 A | 2/1999 |
| JP | 2000-046640 A | 2/2000 |
| JP | 2000-131135 A | 5/2000 |
| JP | 2004-080475 A | 3/2004 |
| WO | 2007/101508 A1 | 9/2007 |

\* cited by examiner

*Primary Examiner* — Nicole F Lavert
(74) *Attorney, Agent, or Firm* — Seed IP Law Group PLLC

(57) ABSTRACT

Disclosed is a frequency analyzer for a MEMS based cochlear implant with self power supply. The frequency analyzer for a MEMS based cochlear implant includes: an upper structure including a first substrate, and a nano wire contact portion formed under the first substrate and coated with a high conductivity metal; and a lower structure including a second substrate having a space filled with a fluid and an upper portion of which is opened, a membrane formed on the fluid filled in the space of the second substrate, a first electrode formed on the membrane, and a nano wire formed on the first electrode and having the piezoelectric characteristics related to an arbitrary direction in which the nano wire is grown.

18 Claims, 20 Drawing Sheets

FREQUENCY ANALYZER FOR MEMS BASED COCHLEAR IMPLANT WITH SELF POWER SUPPLY

BACKGROUND

1. Technical Field

The present invention relates to a frequency analyzer for a MEMS based cochlear implant with self power supply, and more particularly, to a frequency analyzer for a MEMS based cochlear implant that enables the cochlear implant without any battery for power supply to be implanted in the human body and has a self power supply function without using conventional complex units such as a microphone, a speech processor, and a wireless electricity supply.

2. Description of the Related Art

As illustrated in FIG. 1, there exist a basilar membrane decomposing sound according to its frequencies and stereocilia disposed at the upper end of the basilar membrane to convert sound information to electrical signals and transmit the electrical signals to the brain through nerves in a cochlea of a mammal.

The typical human cochlea operates over a 3-decade frequency band, from 20 Hz to 20 kHz, covers 120 dB of dynamic range, and can distinguish tones that differ by less than 0.5%. The cochlea is also very small and occupies a volume of approximately 1 cm$^3$. Perhaps most importantly, the cochlea uses a mechanical process to separate audio signals into approximately 3,500 channels of frequency information. Thus, the cochlea is a sensitive real-time mechanical frequency analyzer.

As illustrated in FIG. 2, the currently used cochlear implant includes a microphone, a speech processor, a transmitter/receiver, and an array of electrodes. The cochlear implant has up to 22 channels. The microphone converts sound wave signals to electrical analog signals, and the speech processor performs signal processing such as conversion of time based electrical analog signals to frequency based electrical digital signals on the basis of the digital signal processor (DSP) technology. The transmitter/receiver wirelessly transmits signals of the speech processor outside the body into the body.

As illustrated in FIG. 3, a basilar membrane in a cochlea has a thick and narrow structure in a base region to be resonated by high-frequency waves and has a thinner and wider flexible structure as it goes toward an apex region.

Thus, as illustrated in FIG. 4, electrodes are inserted into a cochlea to stimulate auditory nerves distributed from the base (high-frequency region) to the apex (low-frequency region), generating bioelectrical signals and transmitting the information to the cochlear nucleus in a brain stem.

However, the conventional cochlear implant system includes a complex structure having a microphone, a speech processor, and a transmitter that are attached outside a human body, and a receiver, a stimulator, and electrodes that are implanted in the human body, so a large and expensive electronic circuit chipset is necessary and a large amount of power is consumed, increasing the price of the entire system. Moreover, a large capacity battery and an auxiliary unit are necessary to generate electrical signals, and in most cases, the lifespan of the battery is limited to from several hours to below one week, requiring frequent recharges of the battery.

Further, since the use of the DSP in the conventional cochlear implant system causes delay of audio signals up to several tens of seconds and the electrical signals are encoded to be wirelessly transmitted to an electronic circuit in the skull, only a limited number of channels can be processed.

Furthermore, a cochlear implant system is practical and its listening quality is most important regardless of its appearance. However, although the cochlear implant systems suggested until now allow the users to distinguish simple spoken words, the users have difficulty in appreciating music and distinguishing tones of languages.

BRIEF SUMMARY

Therefore, the present invention has been made in view of the above problems, and it is an aspect of the present invention to provide a frequency analyzer for a MEMS based cochlear implant that enables the cochlear implant without any battery for power supply to be implanted in the human body and has a self power supply function without using conventional complex units such as a microphone, a speech processor, and a wireless electricity supply.

It is another aspect of the present invention to provide a frequency analyzer for a MEMS based cochlear implant with self power supply, comprising: an upper structure including a first substrate, and a nano wire contact portion formed under the first substrate and coated with a high conductivity metal; and a lower structure including a second substrate having a space filled with a fluid and an upper portion of which is opened, a membrane formed on the fluid filled in the space of the second substrate, a first electrode formed on the membrane, and a nano wire formed on the first electrode and having piezoelectric characteristics related to an arbitrary direction in which the nano wire is grown.

The frequency analyzer may further comprise: a sound wave entrance functioning as a passage for, upon generation of sound waves in the lower structure, allowing the sound waves to cause the fluid filled in the space of the lower structure to flow.

The first substrate may be a silicon wafer.

The nano wire contact portion may include a saw tooth formed immediately under the first substrate and made of silicon or a polymer and a coating portion coating an outer region of the saw tooth with a conductive thin film.

The saw tooth of the nano wire contact portion may have a polygonal shape such as a triangular shape.

A plurality of first electrodes may be continuously formed, but the intervals between, the widths of, and the lengths of the first electrodes may be different such that input sound waves are properly transferred.

The first electrode may be formed on the membrane, at the lower end of the membrane, or in the middle of the membrane, and the nano wire may be located on the first electrodes or on the conductive membrane.

A signal line may be formed in the first electrode connected to the nano wire and may be connected to an insertion type electrode channel of a cochlea.

One or more nano wires may be formed such that when the nano wires make contact with the saw teeth of the upper structure, the nano wires are bent so as to generate current and the electrical signal is transmitted to the insertion type electrode channel of a cochlea to simulate the auditory nerves.

A signal amplifier or a sound processor may be connected between the first electrode and the insertion type electrode channel of a cochlea.

The nano wire may be grown on the first electrode perpendicular to the first electrode or at an arbitrary angle.

The nano wire may be made of one of ZnO, ZnMgO, PMN-PT, PZN-PT, PVDF, PVC, PAN, and PZT.

The membrane may be made of a polymer or a polymer complex material.

The saw tooth may be manufactured by a semiconductor process or a nano imprinting process.

The fluid may be silicon oil that exists in a cochlea.

A third substrate made of Si3N4 and a fourth substrate made of a polymer to surround the third substrate may be provided between the space of the lower structure 200 and the first electrode.

The sound wave entrance may be connected to one of three ossicle bones connected to an eardrum membrane.

The frequency analyzer for a MEMS based cochlear implant according to the present invention enables the cochlear implant without any battery for power supply to be implanted in the human body and has a self power supply function without using conventional complex units such as a microphone, a speech processor, and a wireless electricity supply.

BRIEF DESCRIPTION OF THE SEVERAL VIEWS OF THE DRAWINGS

The above and other aspects, features and other advantages of the present invention will be more clearly understood from the following detailed description taken in conjunction with the accompanying drawings, in which.

DETAILED DESCRIPTION

Hereinafter, preferred embodiments of the present invention will be described in detail with reference to the accompanying drawings.

Figure 1:
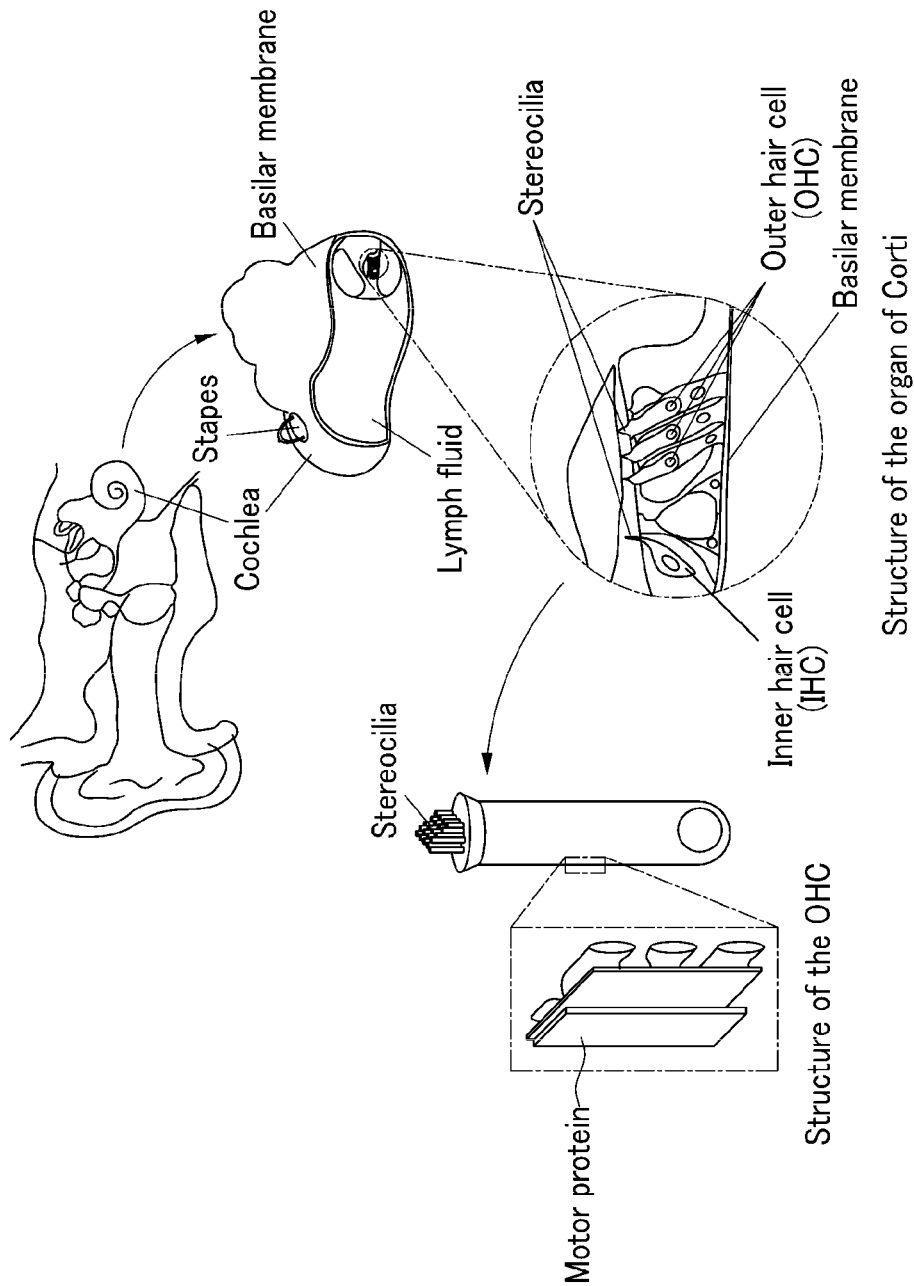
FIG. 1 is a view illustrating a cross-section of a general cochlea and the structure of stereocilia.
Figure 2:
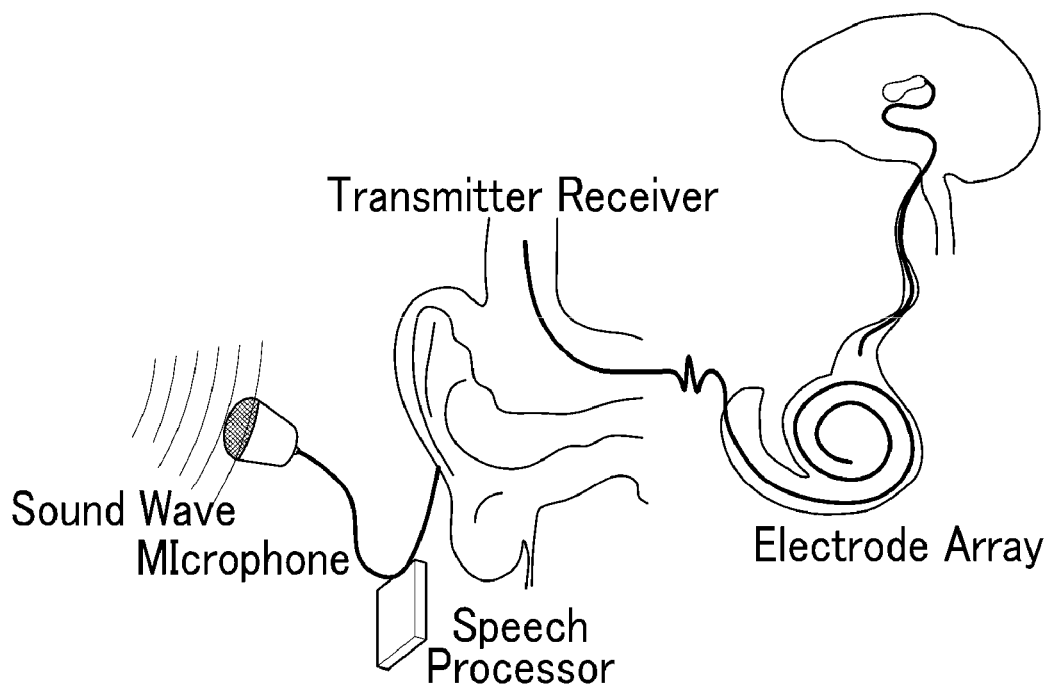
FIG. 2 is a view illustrating a conventional cochlear implant system.
Figure 3:
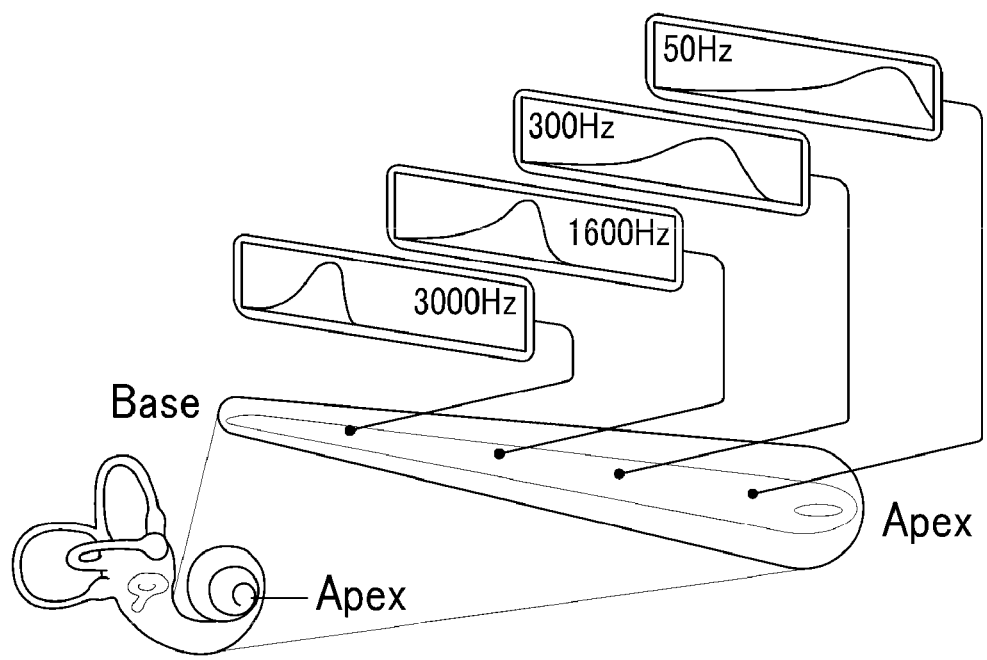
FIG. 3 is a view illustrating perception of frequencies in a basilar membrane of a cochlea.
Figure 4:
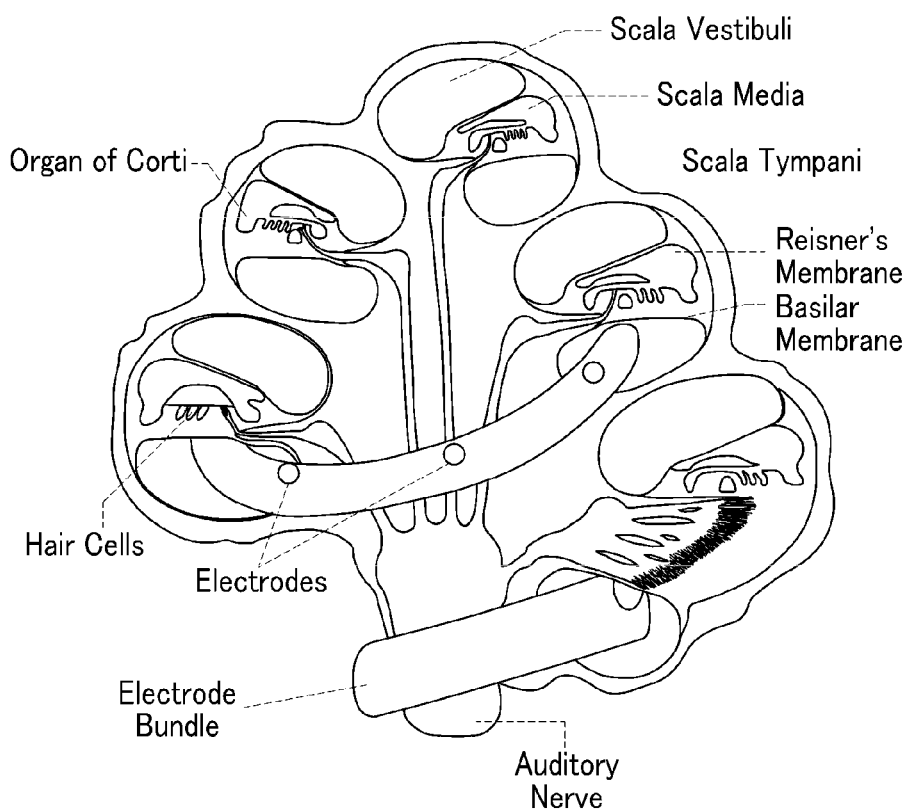
FIG. 4 is a view illustrating insertion of electrodes into a cochlea.
Figure 5A:
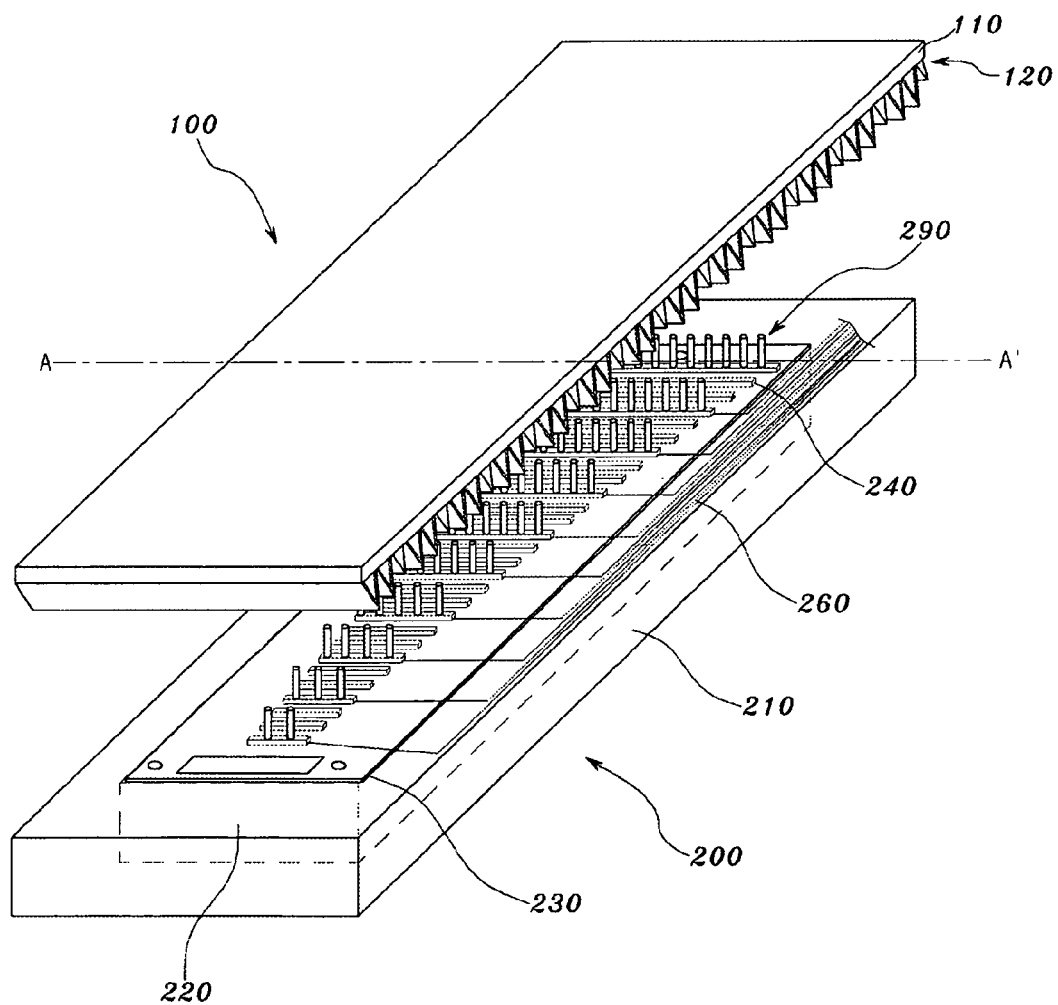
FIG. 5A is a perspective view illustrating a frequency analyzer for a cochlear implant according to an embodiment of the present invention.
Figure 5B:
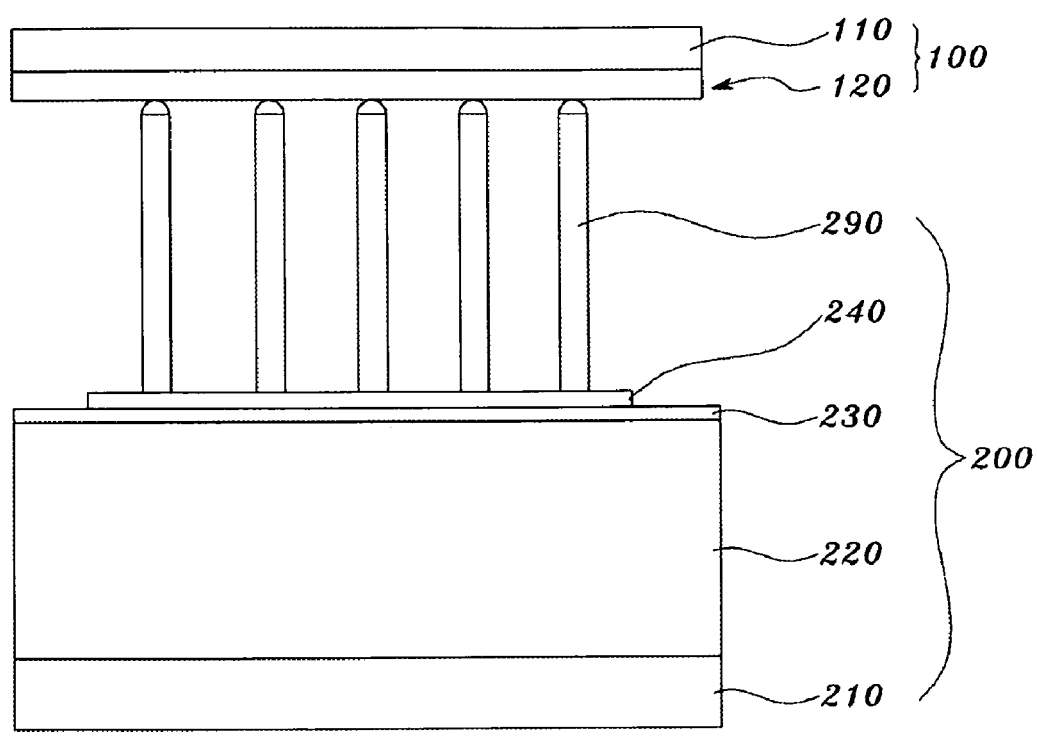
FIG. 5B is a sectional view taken along line A-A' of FIG. 5A.

FIG. 5A is a perspective view illustrating a frequency analyzer for a cochlear implant according to an embodiment of the present invention. FIG. 5B is a sectional view taken along line A-A' of FIG. 5A.

Referring to FIGS. 5A and 5B, the frequency analyzer for a MEMS cochlear implant with self power supply according to the embodiment of the present invention mainly includes an upper structure 100 and a lower structure 200.

The upper structure 100 includes a first substrate 110, and saw-toothed nano wire contact portions 120 formed under the first substrate 110.

Each nano wire contact portion 120 has a saw tooth that directly makes contact with a nano wire 290, and the outermost side of the saw tooth is coated with a high conductivity metal such as platinum. As illustrated in FIG. 5A, a plurality of saw teeth are continuously disposed along the length of the upper structure 100.

The lower structure 200 includes a second substrate 210, a membrane 230, first electrodes 240, and nano wires 290 sequentially from the lower to upper portions thereof.

Each nano wire 290 has piezoelectric and semiconductor characteristics related to an arbitrary direction in which it is grown.

In the embodiment of the present invention, when the upper structure 100 is stacked on the lower structure 200, the nano wires 290 of the lower structure 200 make contact with the nano wire contact portions 120 of the upper structure 100.

Next, the upper and lower structures will be described in detail with reference to FIGS. 6 and 7.

Figure 6A:
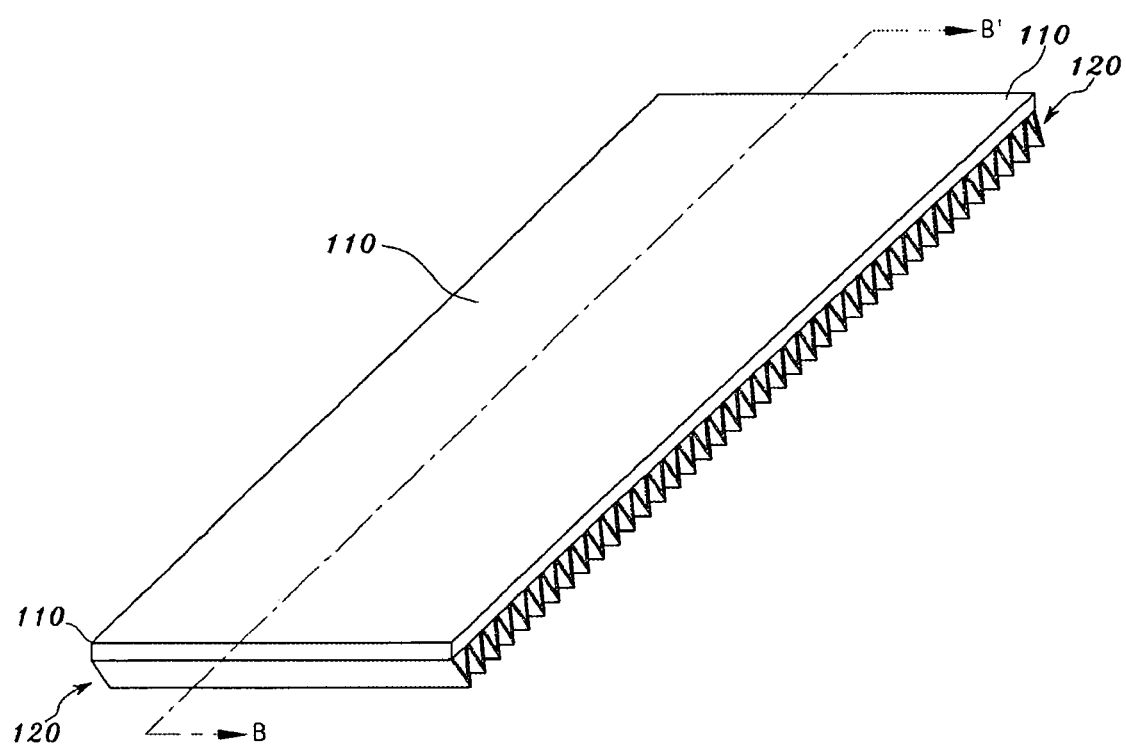
FIG. 6A is a perspective view illustrating an upper structure of the frequency analyzer for a cochlear implant according to the embodiment of the present invention.
Figure 6B:
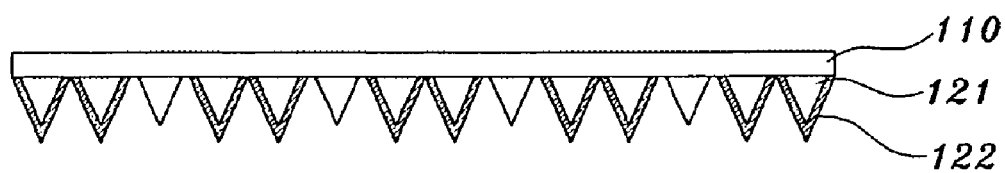
FIG. 6B is a sectional view taken along line B-B' of FIG. 6A.
Figure 7A:
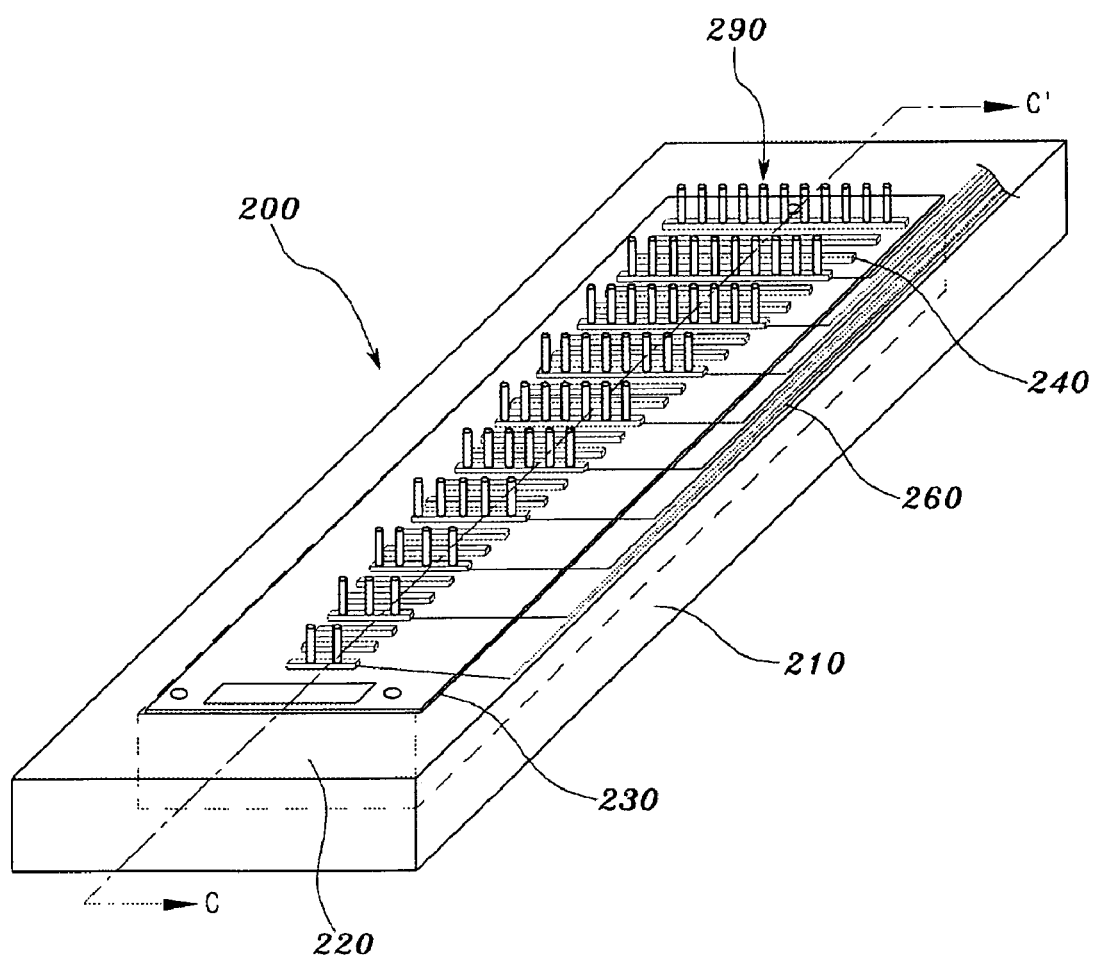
FIGS. 7A to 7C are a perspective view, a sectional view (taken along line C-C' of FIG. 7A), and a plan view of a lower structure of the frequency analyzer for a cochlear implant according to the embodiment of the present invention respectively.
Figure 7B:
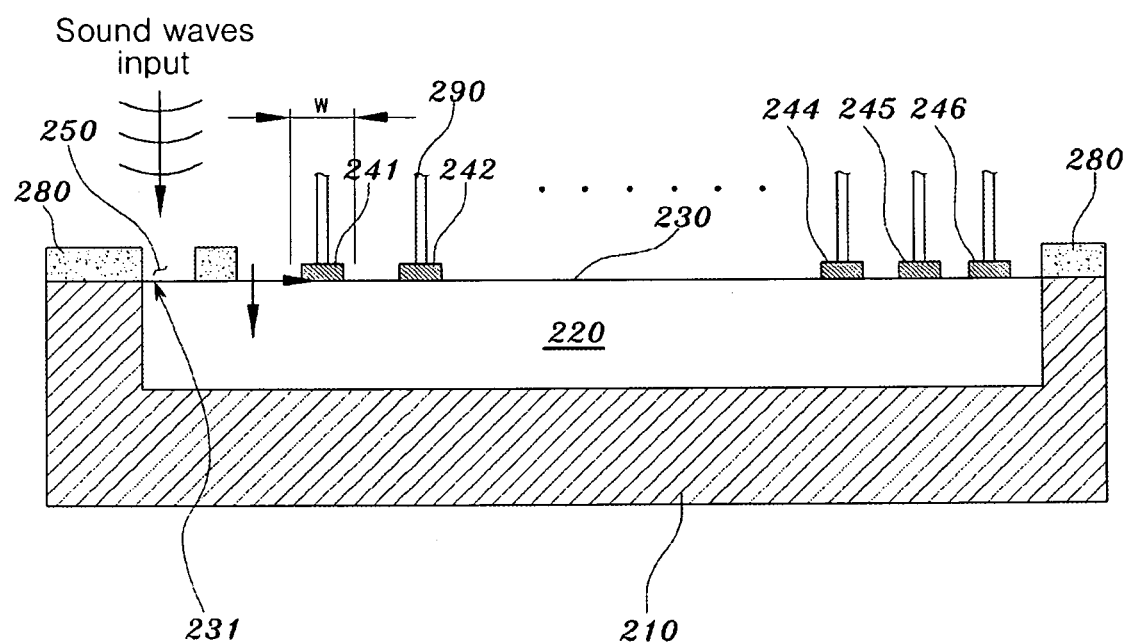
Figure 7C:
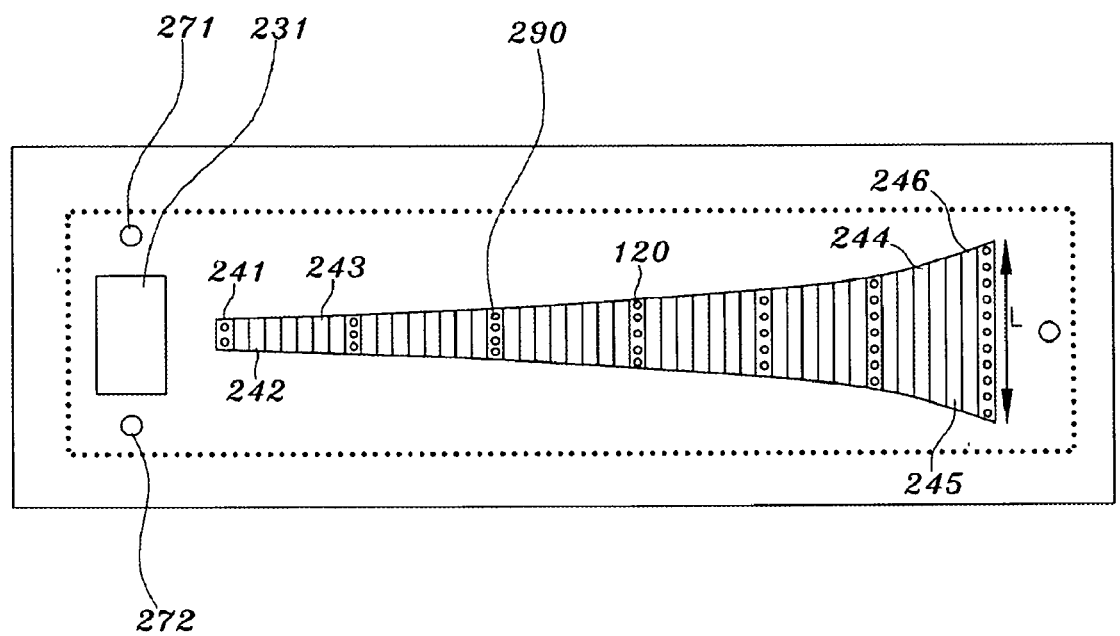
Figure 7D:
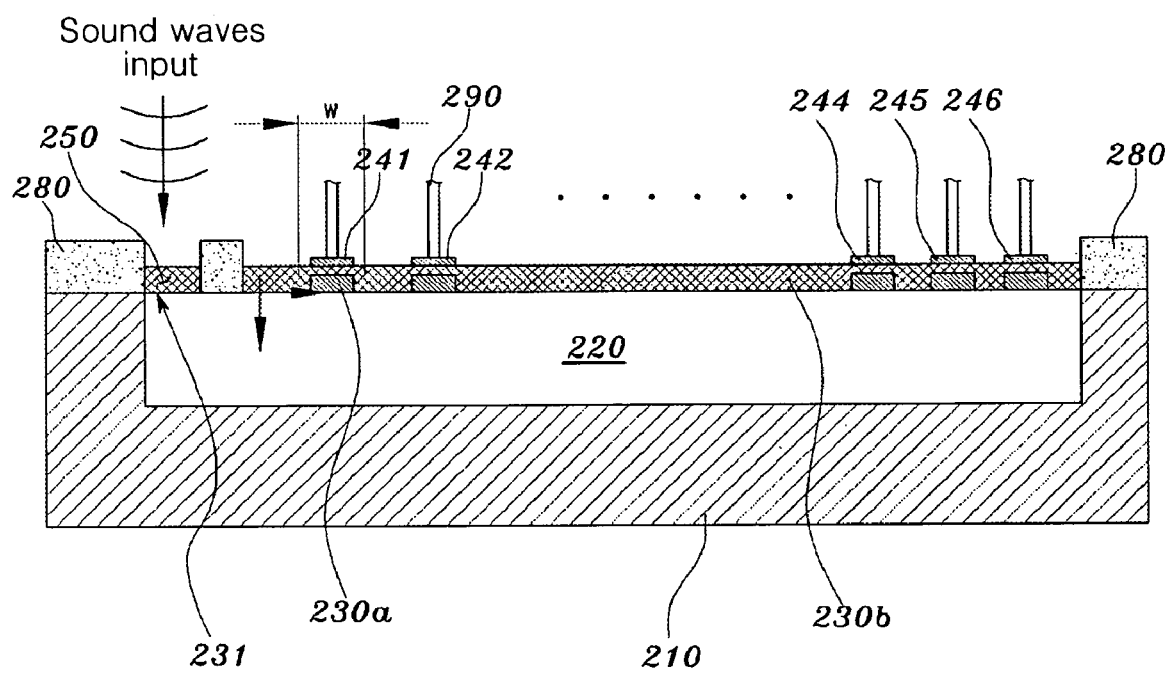
FIG. 7D is a view illustrating FIG. 7B in more detail.

FIG. 6A is a perspective view illustrating an upper structure of the frequency analyzer for a cochlear implant according to the embodiment of the present invention. FIG. 6B is a sectional view taken along line B-B' of FIG. 6A. FIGS. 7A to 7B are a perspective view, a sectional view (taken along line C-C' of FIG. 7A), and a plan view of a lower structure of the frequency analyzer for a cochlear implant according to the embodiment of the present invention respectively. FIG. 7D is a view illustrating FIG. 7B in more detail.

First, the upper structure will be described with reference to FIGS. 6A and 6B.

As mentioned above, the upper structure 100 includes a first substrate 110, and saw-toothed nano wire contact portions 120 formed under the first substrate 110.

Preferably, the first substrate 110 is a silicon wafer.

The nano wire contact portions 120 may be saw-toothed, and the outermost sides of the saw teeth are coated with a high conductivity metal. In other words, each nano wire contact portion 120 includes a saw tooth 121 formed under the first substrate 110 and made of silicon, and a coating portion 122 coating an outer region of the saw tooth 121 that makes contact with a nano wire 290 with a high conductivity metal. The first substrate 110 and the saw teeth 121 may be integrally formed, for they are made of the same material.

In the embodiment of the present invention, the outermost part of each nano wire contact portion 120, i.e., the coating portion of a high conductivity metal makes contact with one end of a nano wire 290. The opposite end of the nano wire 290 is connected to a first electrode 240 that will be described later.

The nano wire contact portions 120 are saw-toothed to allow easy contact with the nano wires 290. In other words, if the nano wire contact portions 120 are saw-toothed, circuits are formed such that current flows from ends of the nano wires 290 to the saw-toothed nano wire contact portions 120 when the nano wires 290 are deformed, but if the nano wire contact portions 120 are flattened, a circuit cannot be formed since current does not flow from ends of the nano wires 290 to the flattened nano wire contact portions 120 even when the nano wires 290 are deformed.

Although the nano wire contact portions 120 are saw-toothed as in FIG. 6B in the embodiment of the present invention, the present invention is not limited thereto and the grooves may have a polygonal shape such as a rectangular shape. More preferably, the shape of the grooves may be triangular. In the embodiment of the present invention, the edges of the triangular grooves of the nano wire contact portions 120 make contact with deformed nano wires 290.

Meanwhile, as illustrated in FIG. 7A, the lower structure 200 includes a second substrate 210, a membrane 230, first electrodes 240, and nano wires 290 sequentially from the lower to upper portions thereof, and the first electrodes 240 are flattened to be distinguished from an electrode channel 300 inserted into a cochlea.

As illustrated in FIG. 7B, the second substrate 210 is made of silicon and has a specific space therein.

A fluid is filled in the space. The fluid may be silicon oil and will be described later.

The membrane 230 is formed on the fluid in the space 220, and is preferably made of a polymer such as polyimide or SU-8, or a polymer complex material including a polymer layer, a nano wire dispersion layer, and a polymer layer.

The membrane 230 moves when the fluid in the space 220 flows.

The first electrodes 240 may be formed on the membrane 230, at the lower end of the membrane 230, or in the middle of the membrane 230. It is apparent that the first electrodes 240 move upward and downward when the fluid in the space 220 and the membrane 230 move.

A plurality of first electrodes 241 to 246 are continuously formed, but the intervals between, the widths of, and the lengths of the electrodes may be different such that input sound waves can properly propagate. In FIG. 7A, the shorter first electrodes 240 correspond to high frequency components, and the longer first electrodes 240 correspond to low frequency components.

The nano wires 290 may be located on the first electrodes 240 or on the electrically conductive membrane, and have the piezoelectric and semiconductor characteristics related to an arbitrary direction in which they are grown.

The nano wires 290 are preferably made of a piezoelectric material such as ZnO, ZnMgO, PMN-PT, PZN-PT, PVDF, PVC, PAN, or PZT.

As mentioned above, in the embodiment of the present invention, when the upper structure 100 is stacked on the lower structure 200, the nano wires 290 of the lower structure 200 make contact with the nano wire contact portions 120 of the upper structure 100. In other words, one end of each nano wire 290 is connected to a nano wire contact portion 120 and the opposite end thereof is connected to a first electrode 240. It is apparent that connection between the nano wires 290 and the nano wire contact portions 120 depends on the types and strengths of input sound waves.

Preferably, the frequency analyzer for a MEMS cochlear implant with self power supply according to the embodiment of the present invention further includes a sound wave entrance 250 that functions as a passage in which the fluid in the space of the lower structure is flowed by sound waves.

In the embodiment of the present invention, more than one nano wire 290 may make contact with one first electrode 240, or none of the nano wires 290 may make contact with one first electrode 240.

Preferably, in the embodiment of the present invention, signal lines 260 connected to an insertion type electrode channel 300 of a cochlea are formed only in the first electrodes 240 directly connected to the nano wires 290.

The reference numeral 280 indicates a member formed on the upper side of an unopened upper potion of the second substrate 210 to function as walls. In the embodiment of the present invention, a space is formed between the member 280 and a first electrode 241, and the space is the above-mentioned sound wave entrance 250.

An upper portion of the second substrate 210 is opened, and the opened portion is the above-mentioned specific space 220.

The frequency analyzer for a cochlear implant having the above-mentioned structure is inserted into a human body.

Referring to FIG. 7D, third substrates 230a made of Si3N4 to transmit sound waves better and a fourth substrate 230b made of a polymer such as polyimide or SU-8 to surround the third substrates are provided between the space 220 of the lower structure 200 and the first electrodes. In other words, in the embodiment of the present invention, the membrane 230 includes the third substrates 230a and the fourth substrate 230b.

Preferably, the member making contact with the second substrate (Si substrate) 210 and functioning as walls is made of the same material as that of the second substrate 210, i.e., silicon.

The first electrodes 241 to 246 made of chrome (Cr) or gold (Au) are located on the fourth substrate 230b.

In the lower structure of FIG. 7D, a specific space is formed in a Si substrate 210 to contain a fluid, the fluid is filled in the space, third substrates are formed of Si3N4 on the fluid to function as a membrane, a fourth substrate made of a polymer such as polyimide or SU-8 surrounds the third substrates, first electrodes 241 to 246 are located on the fourth substrate, and nano wires are grown on the first electrodes 241 to 246.

Accordingly, if sound waves are generated, the sound waves passes through the sound wave entrance 250 and the membrane 231 formed in the sound wave entrance 250 to cause the fluid 220 to flow. Then, the membrane 230 including the third substrate 230a and the fourth substrate 230b moves, and the sound waves are transmitted to the first electrodes 240 on the membrane 230, thus deforming the nano wires 290 contacted with the first electrodes 240.

Figure 8A:
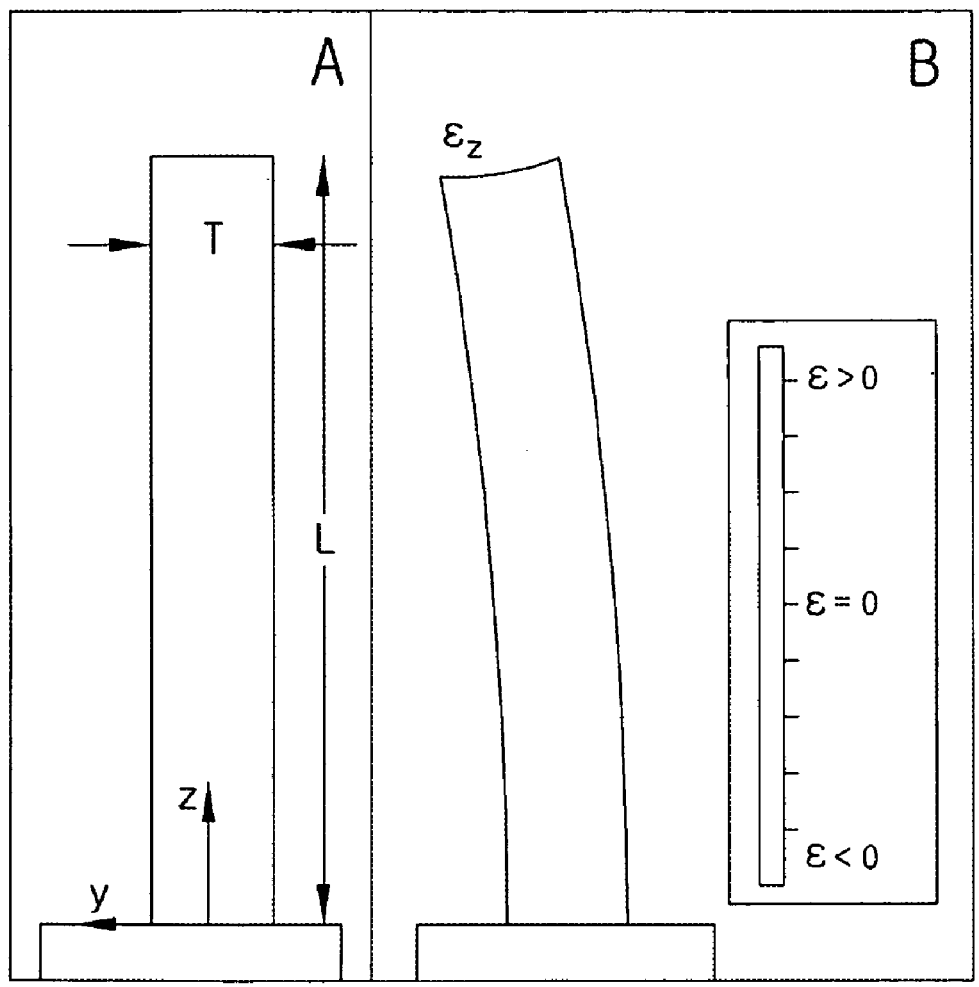
FIG. 8A is a view illustrating the deformation characteristics of a piezoelectric (for example, ZnO) nano wire according to the embodiment of the present invention.
Figure 8B:
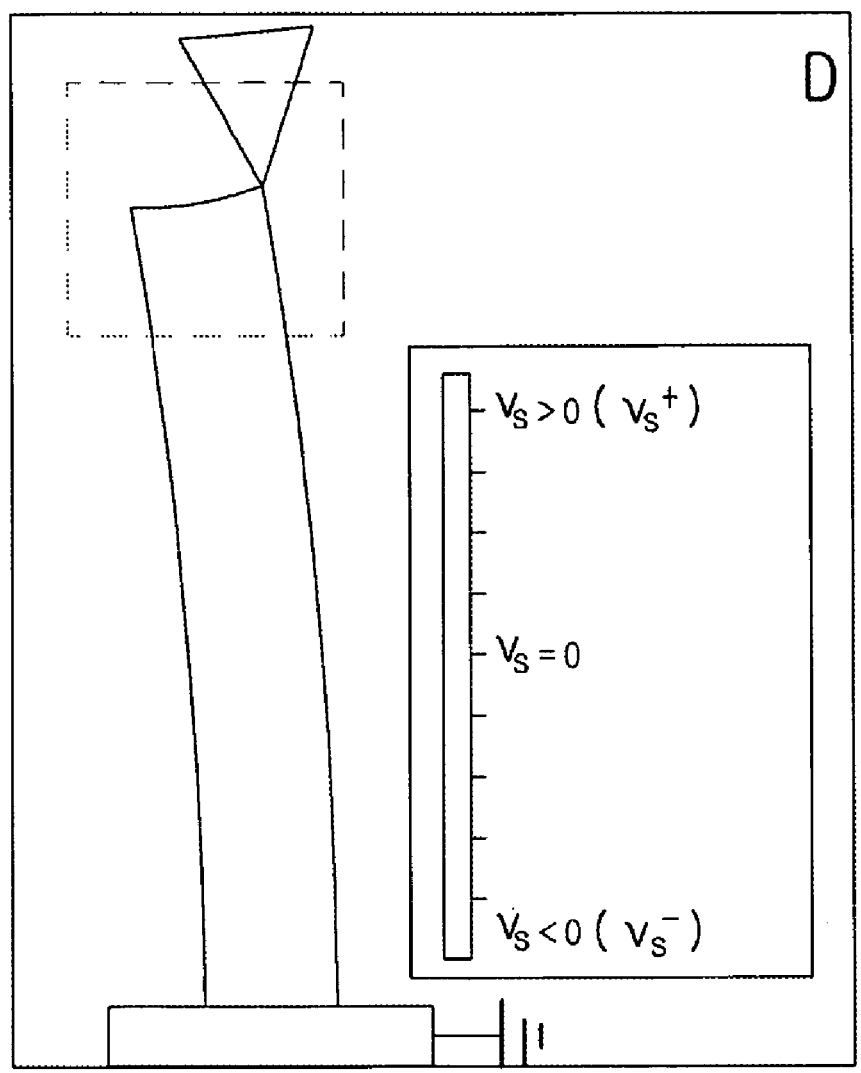
FIG. 8B is a view illustrating the piezoelectric characteristics of the ZnO nano wire according to the embodiment of the present invention.
Figure 8C:
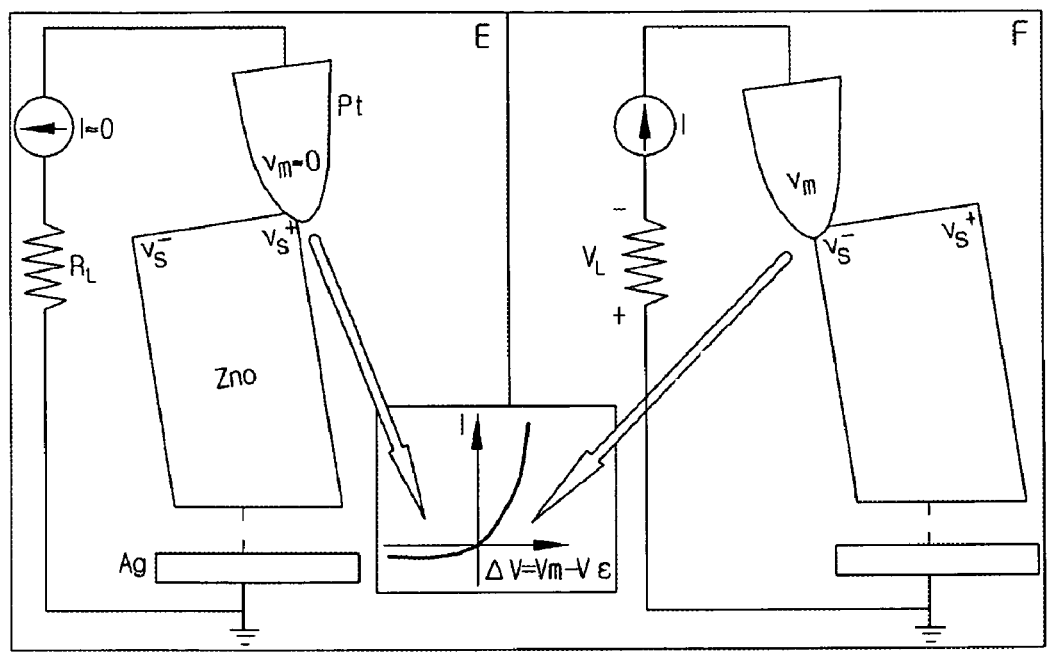
FIG. 8C is a view illustrating the piezoelectric and semiconductor characteristics of the ZnO nano wire according to the embodiment of the present invention.

FIG. 8A is a view illustrating the deformation characteristics of a piezoelectric (for example, ZnO) nano wire according to the embodiment of the present invention. FIG. 8B is a view illustrating the piezoelectric characteristics of the ZnO nano wire according to the embodiment of the present invention. FIG. 8C is a view illustrating the piezoelectric and semiconductor characteristics of the ZnO nano wire according to the embodiment of the present invention.

Recently, Zhong Lin Wang et al. have demonstrated a nanogenerator capable of converting mechanical and vibration energy into electrical energy using the piezoelectric characteristics of ZnO nano wires. (Zhong Lin Wang and Jinhui Song, Piezoelectric Nanogenerators based on Zinc Oxide Nanowire Arrays, 2006, Science, Vol. 312)

As illustrated in FIG. 8A, if a nano wire is deformed with an AFM tip, a tensile region and a compressive region are generated in the nano wire, and as illustrated in FIG. 8B, a positive potential is applied to the tensile region and a negative potential is applied to the compressive region due to the piezoelectric characteristics of the nano wire.

As illustrated in FIG. 8C, when the ground is connected to a base and a tungsten tip makes contact with a positive potential in a tensile region of the apex of a nano wire, the nano wire functions as a reverse bias schottky diode to prevent flow of current. On the other hand, when the tungsten tip makes contact with a negative potential in a compressive region, the nano wire functions as a forward bias short key diode to allow flow of current. Accordingly, it is proven that if the ZnO nano wire is deformed, it has piezoelectric and semiconductor characteristics.

Figure 9A:
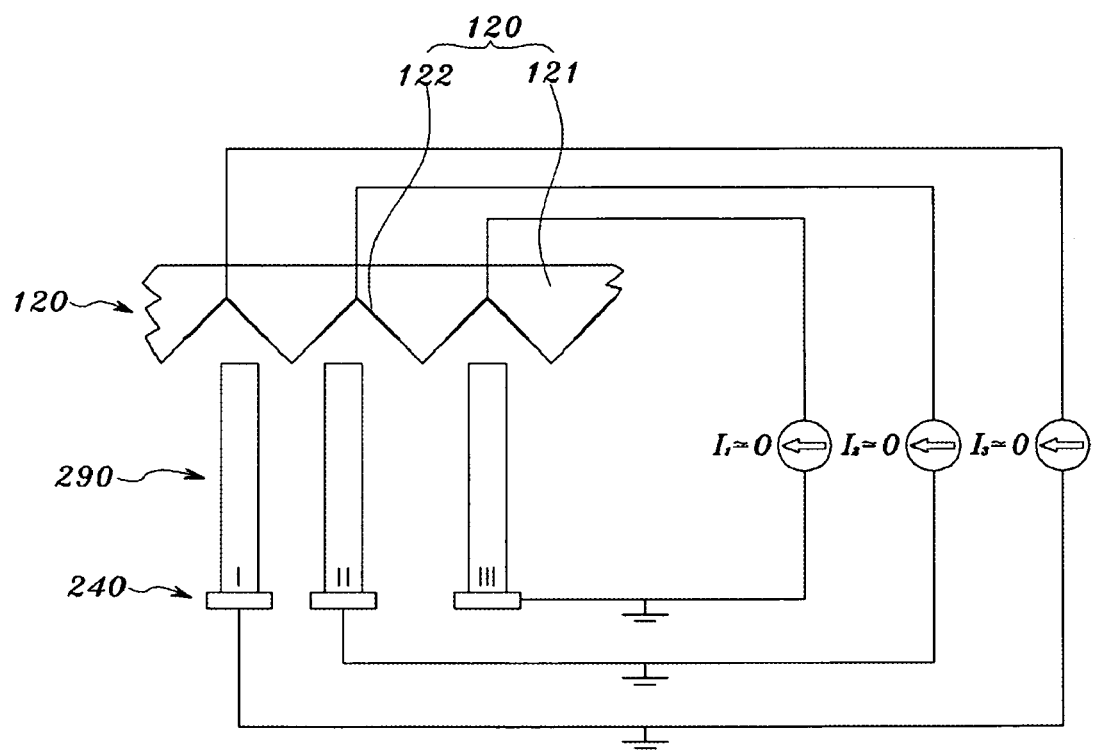
FIGS. 9A and 9B are views illustrating generation of electrical signals in a ZnO nano wire array structure of the frequency analyzer for a cochlear implant according to the embodiment of the present invention.
Figure 9B:
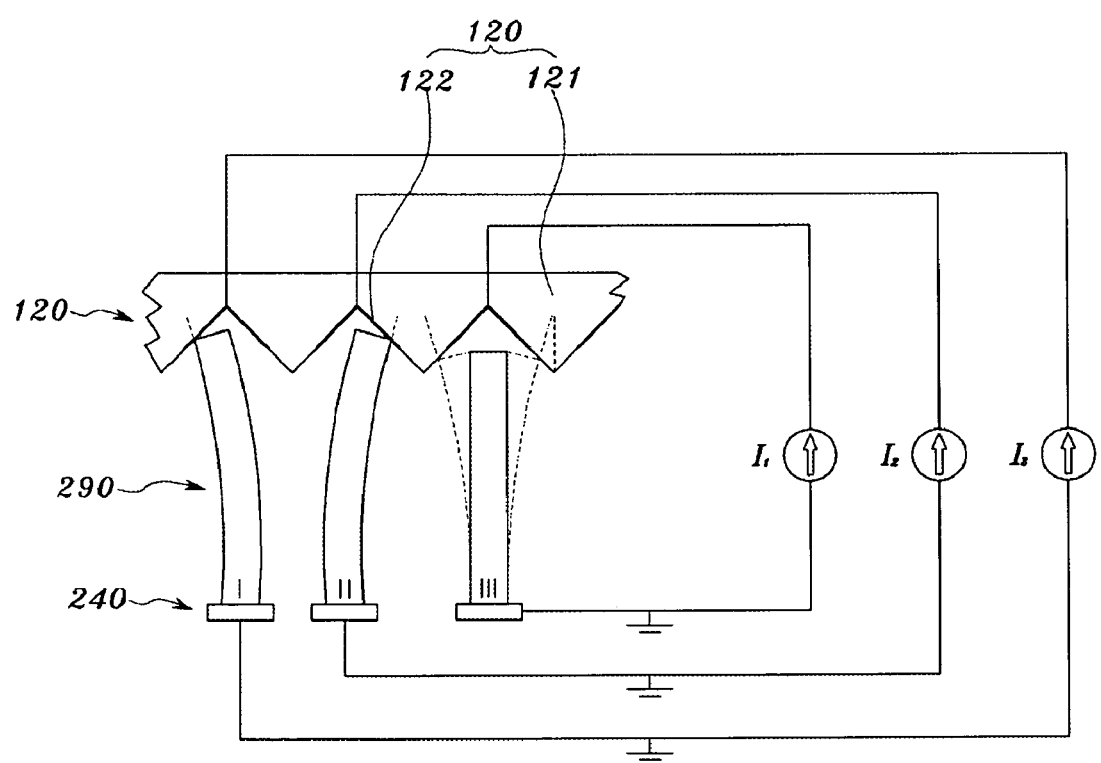
Figure 10:
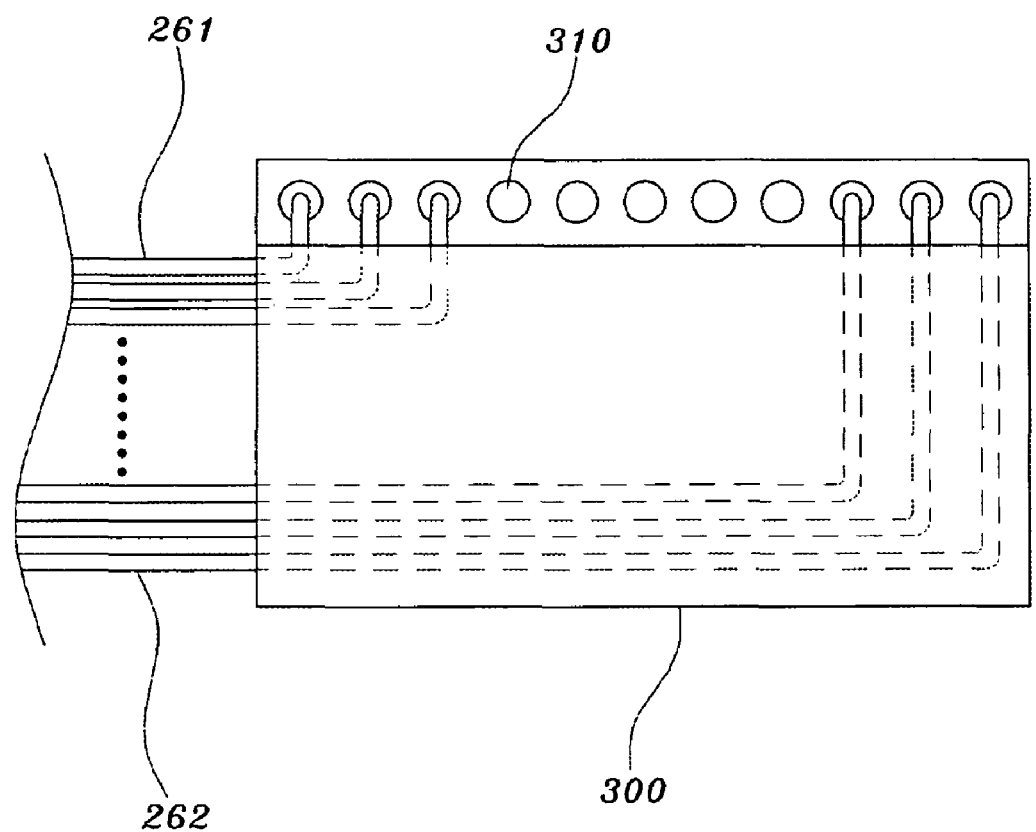
FIG. 10 illustrates transmission of electrical signals generated by deformation of the nano wires of the frequency analyzer for a cochlear implant to an insertion type electrodes channel of a cochlea through signal lines.

FIGS. 9A and 9B are views illustrating generation of electrical signals in a ZnO nano wire array structure of the frequency analyzer for a cochlear implant according to the embodiment of the present invention. FIG. 9A illustrates a state before sound waves are transferred to a fluid, and FIG. 9B illustrates a state after sound waves are transferred to the fluid. FIG. 10 is a view of transmission of electrical signals generated by deformation of the nano wires of the frequency analyzer for a cochlear implant to an insertion type electrodes channel of a cochlea through signal lines.

Referring to FIG. 9A, sound waves are not yet transferred, and ends of the nano wires are not in contact with the nano wire contact portions 120.

If sound waves are transferred, the state of FIG. 9A is converted to the state of FIG. 9B. In other words, if sound waves are transferred, the nano wires 290 are deformed and ends of the nano wires 290 make contact with the nano wire contact portions 120. Accordingly, current (I) flows.

Hereinafter, the operation of the frequency analyzer for a cochlear implant that is illustrated in FIGS. 5 to 7 will be described in more detail with reference to FIGS. 9 and 10.

First, if sound waves are generated, they pass through the sound wave entrance of the lower structure and the membrane 231 formed in the sound wave entrance to cause the fluid 220 of the lower structure to flow. Then, the membrane 230 also moves, and the sound waves are transferred to the first electrodes 240 on the membrane 230, thus deforming the nano wires 290 contacted with the first electrodes 240. The deformed nano wires 290 make contact with the nano wire contact portions 120 of the upper structure, thus generating electrical signals (currents (I)). The electrical signals are transmitted to the insertion type electrode channel 300 through the signal lines 261 and 262, and stimulate the auditory nerves of hair cells through auditory nerve stimulating electrodes 310 of the insertion electrode channels of a cochlea.

In FIG. 10, the reference numeral 261 indicates a high frequency signal line, and the reference numeral 262 is a low frequency signal line.

Figure 11A:
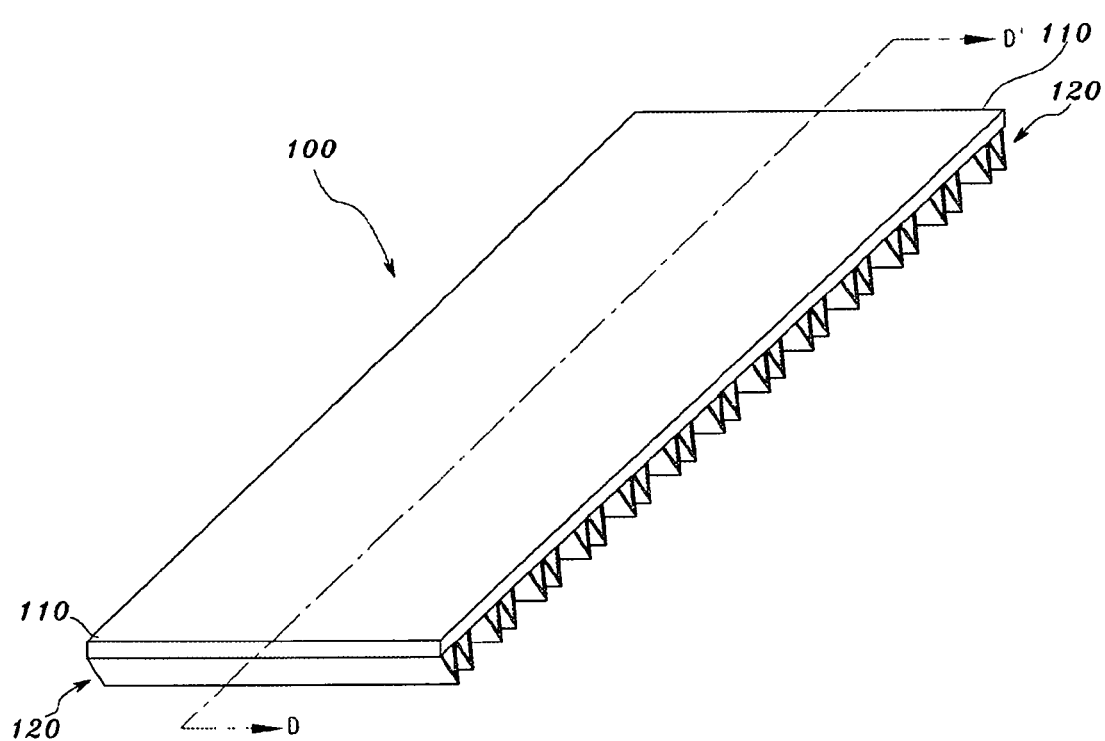
FIG. 11A is a perspective view illustrating an upper structure according to another embodiment of the present invention.
Figure 11B:
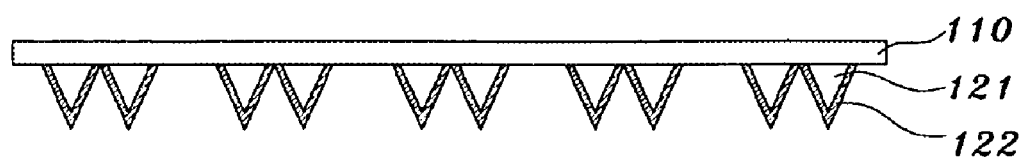
FIG. 11B is a sectional view taken along line D-D' of FIG. 11A.

FIG. 11A is a perspective view illustrating an upper structure according to another embodiment of the present invention. FIG. 11B is a sectional view taken along line D-D' of FIG. 11A.

As illustrated in FIG. 11, in the embodiment of the present invention, the coating portions of the upper structure of FIG. 6 are modified.

More particularly, the upper structure 100 according to the embodiment of the present invention includes a first substrate 110, and saw-toothed nano wire contact portions 120 formed under the first substrate 110. The saw-teeth may be formed by nano imprinting.

Each nano wire contact portion 120 includes a saw-tooth 121 made of silicon and formed immediately under the first substrate 110, and a coating portion 122 coating an outer region of the saw tooth 121 with a high conductivity metal such as platinum.

The difference between FIG. 6 and FIG. 11 lies in the shape of the coating portions. In other words, while the saw teeth are continuously formed and only the regions of the coating portions that make contact with the nano wires are coated in FIG. 6, the saw teeth of the coating portions are discontinuously formed in FIG. 11. Only the regions contacted with the nano wires are coated or the saw teeth of the coating portions are discontinuously formed to interrupt electrical contact between the nano wires contacted with the coating portions. In other words, since if adjacent nano wires make contact with each other, problems are caused in the system, the saw teeth are discontinuously and intermittently formed to prevent problems.

It is apparent that, as another method for interrupting electrical contact between nano wires, platinum may be coated on the portions of the nano wire contact portions that directly make contact with the nano wires in FIG. 6B.

In the embodiment of the present invention, the fluid filled in the space preferably is a fluid having the same characteristics as those of the fluid existing in an actual cochlea or a fluid having the characteristics suitable for functioning as a cochlear implant.

The frequency analyzer for a cochlear implant according to the embodiment of the present invention may further include air exits 271 and 272 for discharging the air in the space to the outside after the fluid such as silicon oil is filled in the space. Moreover, the air exits also function as passages for injection of the fluid.

After the fluid is injected into the air exits 271 and 272, the air outlets 271 and 272 are sealed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A frequency analyzer for a MEMS based cochlear implant, comprising:
    an upper structure including a first substrate, and a nano wire contact portion formed under the first substrate and coated with a high conductivity metal; and
    a lower structure including a second substrate having a space filled with a fluid and an upper portion of which open, a membrane on the fluid filled in the space of the second substrate, a first electrode on the membrane, and a nano wire on the first electrode, the nano wire having piezoelectric characteristics related to an arbitrary direction in which the nano wire is grown,
    wherein the nano wire is selectively operable to be deformed by movement of the membrane caused by a flow of the fluid, and the deformed nano wire contacts the nano wire contact portion of the upper structure, thereby generating an electrical signal.

2. The frequency analyzer according to claim 1, further comprising:
    a sound wave entrance functioning as a passage for sound waves, allowing the sound waves to cause the fluid filled in the space of the lower structure to flow.

3. The frequency analyzer according to claim 1, wherein the first substrate is a silicon wafer.

4. The frequency analyzer according to claim 1, wherein the nano wire contact portion includes a saw tooth immediately under the first substrate and made of silicon or a polymer and a coating portion coating an outer region of the saw tooth with a conductive thin film.

5. The frequency analyzer according to claim 4, wherein the saw tooth of the nano wire contact portion has a polygonal shape such as a triangular shape.

6. The frequency analyzer according to claim 1, wherein a plurality of first electrodes are provided with intervals between, widths, and lengths that are different.

7. The frequency analyzer according to claim 1, wherein the first electrode is on the membrane, at a lower end of the membrane, or in a middle of the membrane, and the nano wire is located on the first electrode or on the conductive membrane.

8. The frequency analyzer according to claim 4, wherein a signal line connects the first electrode an insertion type electrode channel of a cochlea.

9. The frequency analyzer according to claim 8, wherein one or more nano wires are on the first electrode, and when the nano wires make contact with the saw teeth of the upper structure, the nano wires bend and generate current and the electrical signal is transmitted to the insertion type electrode channel of a cochlea to simulate the auditory nerves.

10. The frequency analyzer according to claim 8, wherein a signal amplifier or a sound processor is connected between the first electrode and the insertion type electrode channel of a cochlea.

11. The frequency analyzer according to claim 1, wherein the nano wire is grown on the first electrode perpendicular to the first electrode or at an arbitrary angle.

12. The frequency analyzer according to claim 11, wherein the nano wire is made of one of ZnO, ZnMgO, PMN-PT, PZN-PT, PVDF, PVC, PAN, and PZT.

13. The frequency analyzer according to claim 1, wherein the membrane is made of a polymer or a polymer complex material.

14. The frequency analyzer according to claim 4, wherein the saw tooth is manufactured by a semiconductor process or a nano imprinting process.

15. The frequency analyzer according to claim 1, wherein the fluid is silicon oil that exists in a cochlea.

16. The frequency analyzer according to claim 1, wherein a third substrate made of Si3N4 and a fourth substrate made of a polymer to surround the third substrate are provided between the space of the lower structure and the first electrode.

17. The frequency analyzer according to claim 2, wherein the sound wave entrance is connected to one of three ossicle bones connected to an eardrum membrane.

18. The frequency analyzer according to claim 1, wherein the nano wire does not contact a nano wire contact portion of the upper structure unless the nano wire is deformed.

* * * * *